(12) United States Patent  (10) Patent No.: US 7,442,672 B2
Muller et al.  (45) Date of Patent: Oct. 28, 2008

(54) PICOLINAMINE DERIVATIVES AND THEIR USE AS FUNGICIDES

(75) Inventors: Benoît Muller, Lyons (FR); Benoît Hartmann, Sainte-Foy-les-Lyon (FR); Stéphanie Gary, Lyons (FR)

(73) Assignee: Bayer Cropscience S.A. (FR)

( * ) Notice: Subject to any disclaimer, the term of this patent is extended or adjusted under 35 U.S.C. 154(b) by 759 days.

(21) Appl. No.: 10/483,526

(22) PCT Filed: Jul. 4, 2002

(86) PCT No.: PCT/EP02/08664

§ 371 (c)(1),
(2), (4) Date: Mar. 22, 2004

(87) PCT Pub. No.: WO03/006469

PCT Pub. Date: Jan. 23, 2003

(65) Prior Publication Data

US 2004/0147514 A1 Jul. 29, 2004

(30) Foreign Application Priority Data

Jul. 10, 2001 (EP) .................................. 01420155

(51) Int. Cl.
*A01N 43/28* (2006.01)
*A01N 43/34* (2006.01)
*A01N 43/80* (2006.01)
*A01N 43/30* (2006.01)
*A01N 43/82* (2006.01)
*A01N 43/38* (2006.01)
*A61K 31/00* (2006.01)

(52) U.S. Cl. .................................... 504/271; 514/210.2
(58) Field of Classification Search .................. 514/277
See application file for complete search history.

(56) References Cited

U.S. PATENT DOCUMENTS 3,228,950 A * 1/1966 Renk et al. .................. 546/291
5,061,713 A 10/1991 Guillaumet et al.
5,616,590 A 4/1997 Maetzke
5,756,524 A 5/1998 Riordan et al.

FOREIGN PATENT DOCUMENTS

FR 2 803 592 7/2001
WO WO 00/26191 5/2000

* cited by examiner

*Primary Examiner*—Johann Richter
*Assistant Examiner*—Courtney Brown
(74) *Attorney, Agent, or Firm*—Ostrolenk, Faber, Gerb & Soffen, LLP

(57) ABSTRACT

Compound of general formula (I), in which: Y and G together with carbon atoms 3 and 4, form a 5 or 6 member ring chosen from the following structures (A) to (F), the other substituents being as defined in the description. Process for preparing this compound. Fungicidal composition comprising this compound. Method for treating plants by applying this compound or composition.

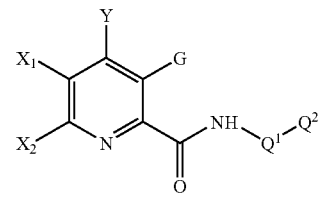

(I)

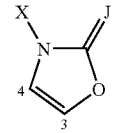

(A)

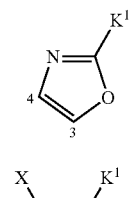

(B)

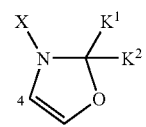

(C)

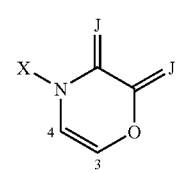

(D)

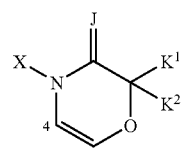

(E)

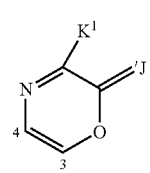

(F)

24 Claims, No Drawings

PICOLINAMINE DERIVATIVES AND THEIR USE AS FUNGICIDES

CROSS REFERENCE TO RELATED APPLICATION

The present application is a 35 U.S.C. § 371 national phase conversion of PCT/EP02/08664, filed Jul. 4, 2002, which claims priority of European Application No. 01420155.2 filed Jul. 10, 2001.

The present invention relates to new derivatives of picolinic acid, their process of preparation, their use as fungicides, particularly in the form of fungicidal compositions, and methods for the control of phytopathogenic fungi of plants using these compounds or their compositions.

Picolinic acid derivatives with fungicidal action are known in the literature. Thus, antimycin and certain derivatives thereof, disclosed in particular in patent application WO-A-99/11127 and by Kuzo Shibata et al. (*The Journal of Antibiotics*, 51 (12), (1998), 1113-1116), are presented as being effective against phytopathogenic fungi of plants, with good efficacy. These compounds, and those disclosed in patent U.S. Pat. No. 3,228,950, have no substituents in position 4 of the pyridine nucleus.

Patent application WO-A-00/26191 presents picolinamide derivatives that are optionally substituted in position 4 with a methoxy radical. Patent application WO-A-95/25723 proposes 3-pyridylcarboxylic acid derivatives.

Picolinamide derivatives are also known from patent application JP-11 228 542. These derivatives are presented as having potential antifungal activities and low toxicity, for use in pharmaceutical products.

Other picolinic acid derivatives are also known from patent application EP-A-0 690 061, in which such compounds are used as synthetic intermediates for the preparation of pyridothiadiazoles.

However, these known compounds have the drawback of being toxic products, which forbids any use of these compounds in agriculture for eradicating phytopathogenic diseases of crops. Furthermore, these compounds are obtained from fermentation musts and have relatively complex chemical structures. Thus, the preparation and purification of these compounds remain demanding and expensive operations, making any industrial synthesis or marketing economically non-viable.

We have now found a new family of picolinic acid derivative which do not possess the above mentioned drawbacks and which have an improved fungicidal activity.

Accordingly, the present invention provides picolinic acid derivative of general formula (I):

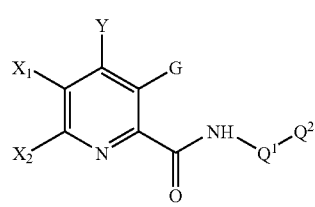

in which:
Y and G together with carbon atoms 3 and 4, form a 5 or 6 member ring chosen from the following structures A to F:

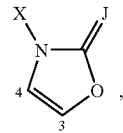
A

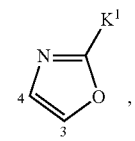
B

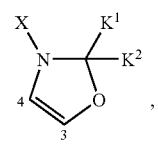
C

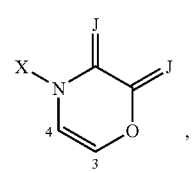
D

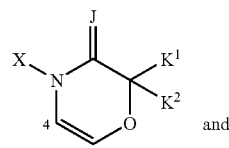
E
and

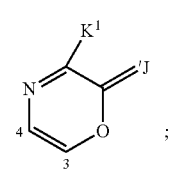
F
;

in which:
J independently represents oxygen or sulphur;
X is chosen in he group consisting of hydrogen, $C_1$-$C_4$ alkyl and $C_1$-$C_4$ halogenoalkyl;
$K^1$ and $K^2$ are identical or different and independently of each other chosen in the group consisting of hydrogen, halogen, $C_1$-$C_4$ allkyl, $C_1$-$C_4$ halogenoalkyl, $C_1$-$C_4$ alkoxyalkyl, $C_1$-$C_4$ alkythioalkyl, —$OR^1$, —$SR^1$, —$SOR^1$, —$SO_2R^1$, —$NHR^3$, —$NR^1R^3$ and

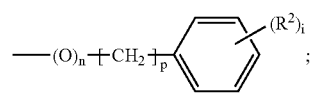
;

$X_1$ and $X_2$ are independently chosen in the group consisting of hydrogen, halogen, —$CF_3$, cyano group and nitro group;
$Q^1$ is chosen in the group consisting of —$(CH_2)_q$—,

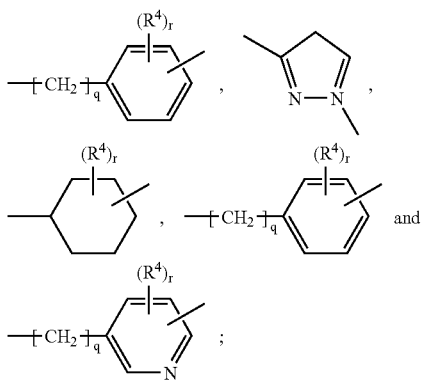

$Q^2$ is chosen in the group consisting of —(O)$_n$—R$^5$, cyano group,

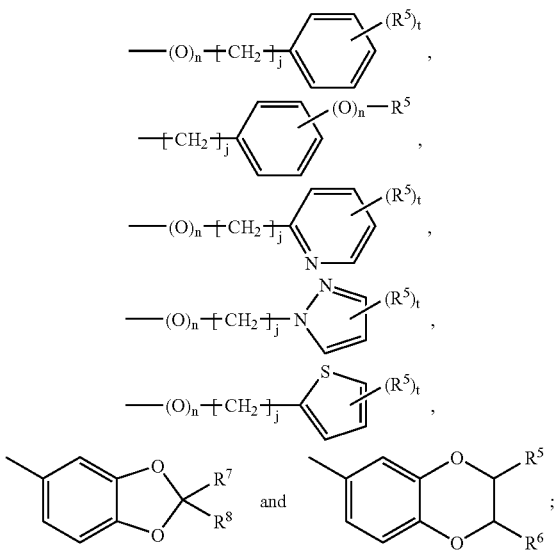

R$^1$ is chosen in the group consisting of hydrogen, C$_1$-C$_4$ alkyl, C$_1$-C$_4$ halogenoalkyl, alkenyl, alkynyl, heterocyclyl, —CH═O, —(C═O)-alkyl and —(C═O)—Oalkyl;

R$^2$ is chosen in the group consisting of halogen, C$_1$-C$_4$ alkyl, C$_1$-C$_4$ alkoxy, C$_1$-C$_4$ halogenoalkyl and aryl;

R$^3$ is chosen in the group consisting of hydrogen, C$_1$-C$_4$ alkyl, C$_1$-C$_4$ halogenoalkyl, C$_1$-C$_4$ alkoxy, alkenyl, alkynyl, heterocyclyl, —CH═O, —(C═O)-alkyl and —(C═O)—Oalkyl;

R$^4$ is chosen in the group consisting of halogen, C$_1$-C$_4$ alkyl and C$_1$-C$_4$ alkoxyalkyl;

R$^5$ and R$^6$ are independently of each other chosen in the group consisting of hydrogen, halogen, C$_1$-C$_4$ alkyl, C$_1$-C$_4$ halogenoalkyl;

R$^7$ and R$^8$ are independently of each other chosen in the group consisting of hydrogen and halogen;

n is 0 or 1;

i, j, p, q and t are independently chosen as being 0, 1, 2, 3 or 4;

r is 0, 1, 2 or 3;

as well as any optional N-oxides, geometrical and/or optical isomers, enantiomers and/or diastereoisomers, tautomeric forms, salts and metal and metalloid complexes of the compounds of formula (I) as here-above defined.

The tautomeric forms of the compound of formula (I) such as those defined above are also included in the invention. By tautomeric forms there are to be understood all of the isomeric forms described in the work "The Tautomerism of Heterocycles, Advances in Heterocyclic Chemistry, Supplement 1, by J Elguero, C. Martin, A. R. Katritsky and P Linda, published by Academic Press, New York, 1976, pages 1-4.

The following generic terms are used with the following meanings in the context of the present invention:

halogen means fluorine, chlorine, bromine or iodine;

alkenyl and alkynyl radicals, as well as groups including such radicals, comprise, unless otherwise indicated, from 2 to 6 carbon atoms in a straight or branched chain and are optionally substituted;

the term "aryl" means phenyl or naphthyl;

the term "heterocyclyl" represents a five or six membered saturated or partially unsaturated or aromatic ring containing one or two heteroatoms of the group N, O, and S which can be identical or different.

Preferably, the present invention relates to picolinic acid derivatives of general formula (I) where the different substituents may be chosen independently from each other as being:

as regards X$^1$ and X$^2$ of general formula (I), each may represent a hydrogen atom;

as regards Y and G of general formula (I), Y and G with carbon 3 and 4, may form a ring chosen from structures A to C;

as regards Q$^1$ of general formula (I), Q$^1$ may be chosen in the group consisting of

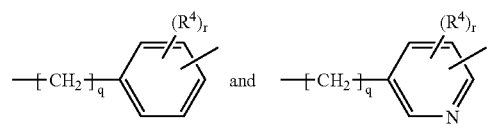

the other substituents being as defined above, as well as the optional N-oxides, geometrical and/or optical isomers, enantiomers and/or diastereoisomers, tautomeric forms, salts and metal and metalloid complexes thereof.

More preferably, the present invention relates to picolinic acid derivatives of general formula (I) as defined above, which have the following characteristics:

X$^1$ and X$^2$ each represent hydrogen,

Y and G together with carbon 3 and 4, form a 5 member ring chosen from structures A to C, Q$^1$ is chosen in the group consisting of

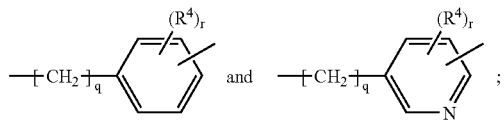

as well as the optional N-oxides, geometrical and/or optical isomers, enantiomers and/or diastereoisomers, tautomeric forms, salts and metal and metalloid complexes thereof.

Even more preferably, the present invention relates to picolinic acid derivatives of general formula (I) as defined above, which have the following characteristics:

X$^1$ and X$^2$ each represent hydrogen,

Y and G together with carbon 3 and 4, form a 5 member ring chosen from:

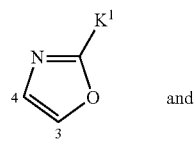

B and

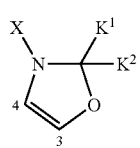

C in which:

X is hydrogen

K$^1$ and K$^2$ are chosen independently of each other from the group consisting of hydrogen, alkyl and N,N-dialkylamino; (R$^4$), (R$^4$), Q$^1$ is chosen in the group consisting of

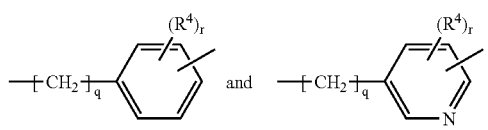

as well as the optional N-oxides, geometrical and/or optical isomers, enantiomers and/or diastereoisomers, tautomeric forms, salts and metal and metalloid complexes thereof.

Even more preferably, the present invention relates to picolinic acid derivatives of general formula (I) as defined above, which have the following characteristics:

X$^1$ and X$^2$ each represent hydrogen,

Y and G together with carbon 3 and 4, may form a 5 member ring of formula A:

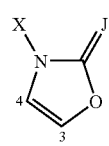

A in which:

J is oxygen,

X is hydrogen;

Q$^1$ is chosen in the group consisting of

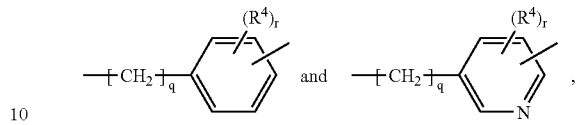

as well as the optional N-oxides, geometrical and/or optical isomers, enantiomers and/or diastereoisomers, tautomeric forms, salts and metal and metalloid complexes thereof.

The compound of general formula (I) can exist in one or more optical isomeric or chiral forms according to the number of asymmetric centres in the compound. The present invention thus also includes all the optical isomers and their racemic or scalemic (scalemic designates a mixture of enantiomers in different proportions), as well as the mixtures of all possible stereoisomers in all proportions, including the racemic mixture. The separation of the diastereoisomers and/or optical isomers can be effected by known methods (E. Eliel ibid.).

The present invention also relates to the process of preparation of the compound of general formula (I). Thus, according to a further aspect of the present invention there is provided a process for the preparation of compound of general formula (I) as defined above which comprises reacting a compound of general formula (II)

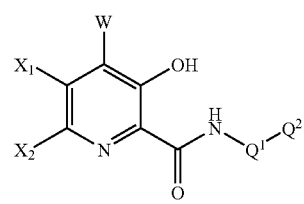

(II)

in which X$^1$, X$^2$, Q$^1$ and Q$^2$ are as defined above and W is NH$_2$ or N$_3$, with a phosgene or thiophosgene solution, an acid halide or a ketone in the presence of solvent.

In particular, a compound according to the general formula (I) having the following structure:

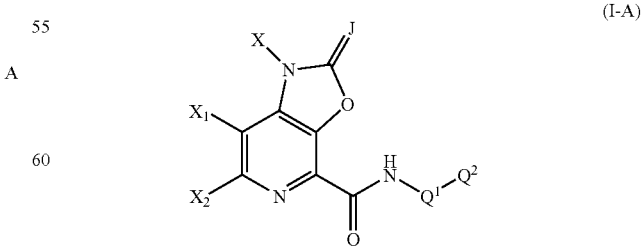

(I-A)

in which J, X, X$^1$, X$^2$, Q$^1$ and Q$^2$ are as defined above, may be prepared by reacting the compound of general formula (II)

where W is NH$_2$ in an apolar aprotic solvent. Suitable solvents include hydrocarbon solvents such as benzene and toluene. The process may be carried out at reflux or at a temperature of between 20° C. and 200° C.

The compound of general formula (I-C):

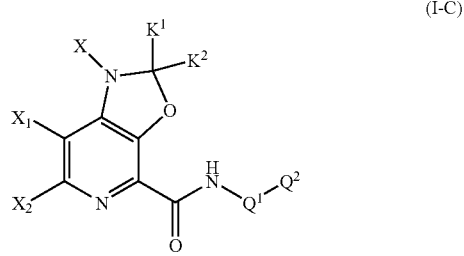

(I-C)

in which X, K$^1$, K$^2$, X$^3$, Q$^1$ and Q$^2$ are as defined above, may be prepared by reacting the compound of general formula (II) in which W is NH$_2$ with alkyl or aryl ketone. The solvent is preferably an apolar aprotic solvent. Suitable solvents include hydrocarbon solvents such as benzene and toluene. The process may be carried out at reflux or at a temperature of between 20° C. and 200° C.

The compound of general formula (I-B):

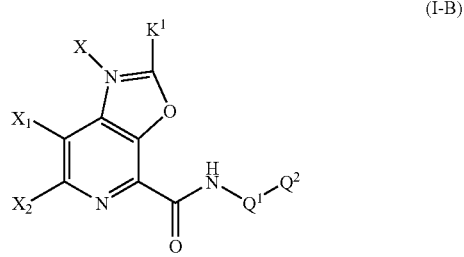

(I-B)

in which K$^1$, X, X$^1$, X$^2$, Q$^1$ and Q$^2$ are as defined above, may be prepared by reacting the compound of general formula (II) where W is NH$_2$ with acid chloride and a base such as triethylamine. The solvent is preferably a chlorinated solvent such as dichloromethane. The process may be carried out at room temperature or at a temperature between −10° C. and +50° C., followed by addition of an amine. Subsequent reduction of the intermediate is obtained with a reducing agents such as triphenyl phosphine or sodium borohydride in an alcoholic solvent such as ethanol or THF.

From these general descriptions, the man skilled in the art will be able to easily prepare the other compounds of formulae (I-D) to (I—F) from the data given in the description and from his general knowledge in organic chemistry.

According to the present invention, it should be understood that the reactions described in the preceding paragraphs may be carried out in any other order, which is suitable to obtain the desired compounds of formula (I). The order of the reactions will be determined most particularly by the compatibility requirements of the various substituents on the pyridine nucleus. Compatibilities of the various radicals and reagents used are well known to the person skilled in the art, who may moreover refer to the examples for the preparation of the compounds of formula (I) described later in this description.

The preparation of reagents used in one or other of the general methods of preparation is generally known and is generally described specifically in the prior art or in such a manner that the man skilled in the art can adapt it to the desired aim. The prior art usable by the normally skilled worker in order to establish conditions for the preparation of reagents can be found in numerous general chemistry text books such as "Advanced Organic Chemistry" by J. March, published by Wiley (1992), "Methoden der organischen Chemie" (Houben-Weyl), published by Georg Thieme Verlag or the "Chemical Abstracts" published by the American Chemical Society as well as in information data bases accessible to the public.

The present invention also relates to fungicidal composition comprising an effective amount of an active material of general formula (I). Thus, according to the present invention, there is provided a fungicidal composition comprising, as an active ingredient, an effective amount of a compound as defined above and an agriculturally acceptable support.

In the present specification, the term "support" denotes a natural or synthetic, organic or inorganic material with which the active material is combined to make it easier to apply to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be between 5% and 40% by weight.

Additional but optional components also include protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention usually may contain from 0.05 to 99% (by weight) of active material.

Compositions according to the present invention can be used in quite diverse forms such as aerosol dispenser, bait (ready for use), bait concentrate, block bait, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, grain bait, granular bait, granule, hot fogging concentrate, macrogranule, microgranule, oil dispersible powder, oil miscible flowable concentrate, oil miscible liquid, paste, plant rodlet, plate bait, powder for dry seed treatment, scrap bait, seed coated with a pesticide, smoke candle, smoke cartridge, smoke generator, smoke pellet, smoke rodlet, smoke tablet, smoke tin, soluble concentrate, soluble powder, solution for seed treatment, suspension concentrate (flowable concentrate), tracking powder, ultra low volume (ulv) liquid, ultra low volume (ulv) suspension, vapour releasing product, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The compounds of the invention can also be mixed with one or more insecticides, fungicides, bactericides, attractant acaricides or pheromones or other compounds with biological activity. The mixtures thus obtained have a broadened spectrum of activity. In particular the compounds of the present invention do not exhibit the problem of cross-resistance with strobilurin derivatives. In fact the compounds of the present invention are active on a different biochemical site to strobilurin derivatives.

The mixtures with other fungicides are particularly advantageous, especially the mixtures with acibenzolar-S-methyl, benalaxyl, benomyl, blasticidin-S, bromuconazole, captafol, captan, carbendazim, carboxin, carpropamide, chlorothalonil, fungicidal compositions based on copper, derivatives of copper such as copper hydroxide and copper oxychloride, cyazofamide, cymoxanil, cyproconazole, cyprodinil, dichloran, diclocymet, diethofencarb, difenoconazole, diflumetorim, dimethomorph, diniconazole, dodemorph, dodine, edifenphos, epoxyconazole, ethaboxam, ethirimol, famoxadone, fenamidone, fenarimol, fenbuconazole, fenhexamide, fenpiclonil, fenpropidine, fenpropimorph, ferirnzone, fluazinam, fludioxonil, flumetover, fluquinconazole, flusilazole, flusulfamide, flutolanil, flutriafol, folpel, furalaxyl, furametpyr, guazatine, hexaconazole, hymexazol, imazalil, iprobenphos, iprodione, isoprothiolane, kasugamycin, mancozeb, maneb, mefenoxam, mepanipyrim, metalaxyl and their enantiomeric forms such as metalaxyl-M, metconazole, metiram-zinc, oxadixyl, pefuirazoate, penconazole, pencycuron, phosphorous acid and its derivatives such as fosetyl-Al, phthalide, probenazole, prochloraz, procymidone, propamocarb, propiconazole, pyrimethaniil, pyroquilon, quinoxyfen, silthiofam, simeconazole, spiroxamine, tebuconazole, tetraconazole, thiabendazole, thifluzamide, thiophanate, for example thiophanate-methyl, thiram, triadimefon, triadimenol, triazolopyrimidines e.g. cloransulam-methyl, flurnetsulam, florasulam, metosulam, tricyclazole, tridemorph, trifloxystrobin, triticonazole, derivatives of valinamide such as for example, iprovalicarb and benthiavalicarb, vinclozolin, zineb and zoxamide, as well as fungicide of the strobilurin familly, for example azoxystrobin, kresoxym-methyl, metominostrobin, discostrobin, dimoxystrobin, picoxystrobin, pyraclostrobin, and trifloxystrobin.

The fungicidal compositions of the present invention can be used to curatively or preventively combat the phytopathogenic fungi of crops. Thus, according to a further aspect of the present invention, there is provided a method for curatively or preventively combating the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be combated, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers and rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants targeted by the method according to the invention, mention may be made of cotton; flax; vine; fruit crops such as *Rosaceae* sp. (for instance pip fruits such as apples and pears, but also stone fruits such as apricots, almonds and peaches), *Ribesioidae* sp., *Juglandaceae* sp., *Betulaceae* sp, *Anacardiaceae* sp., *Fagaceae* sp., *Moraceae* sp., *Oleaceae* sp., *Actinidaceae* sp.,*Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruits); leguminous crops such as *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); big crops such as *Graminae* sp. (for instance maize, cereals such as wheat, rice, barley and triticale), *Asteraceae* sp. (for instance sunflower), *Cruciferae* sp. (for instance colza), *Papilionaceae* sp. (for instance soja), *Solanaceae* sp. (for instance potatoes), *Chenopodiaceae* sp. (for instance beetroots); horticultural and forest crops; as well as genetically modified homologues of these crops.

Among the plants and the possible diseases of these plants targeted by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graininis*), foot blight (*F. culmorum, F. graminearum*), black speck (*Rhizoctonia cerealis*), powdery mildew (*Erysiphe graminis forma specie tritici*), rusts (*Puccinia striiformis* and *Puccinia recondita*) and septoria diseases (*Septoria tritici* and *Septoria nodorum*);

wheat and barley, as regards controlling bacterial and viral diseases, for example barley yellow mosaic;

barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis forma*

*specie hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Phytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding crops, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing crops, for example rape, as regards controlling the following seed diseases: *Phoma lingam, Alternaria brassicae* and *Sclerotinia sclerotiorum;* corn, as regards controlling seed diseases: (*Rhizopus* sp., *Penicillium* sp., *Trichoderma* sp., *Aspergillus* sp., and *Gibberella fujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous crops, as regards controlling the following diseases of seeds or of young plants grown from seeds: damping-off and collar rot (*Fusarium oxysporum, Fusarium roseum, Rhizoctonia solani, Pythium sp.*);

leguminous crops, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae, M. laxa*), scab (*Venturia inaequalis*), powdery mildew (*Podosphaera leucotricha*);

vine, as regards diseases of the foliage: in particular grey mould (*Botrytis cinterea*), powdery mildew (*Uncinula necator*), black rot (*Guignardia biwelli*) and mildew (*Plasmopara viticola*);

beetroot, as regards the following diseases of the aerial parts: cercospora blight (*Cercospora beticola*), powdery mildew (*Erysiphe beticola*), leaf spot (*Ramularia beticola*).

Cereals are preferably treated according to the method of the present invention. Wheat and rice are still preferred for carrying out the method according to the invention.

The fungicide composition according to the present invention may also be used against fungal diseases liable to grow on or inside lumber. The term "lumber" means all types of species of wood, and all types of working of this wood intended for construction, for example solid wood, high-density wood, laminated wood, and plywood. The method for treating lumber according to the invention consists in placing one or more compounds of the present invention, or a composition according to the invention, in contact. This placing in contact may cover the most diverse of forms such as, for example, direct application, spraying, dipping, injection or any other suitable means.

The dose of active material applied in the treatment according to the present invention is generally and advantageously between 10 and 800 g/ha, preferably between 50 and 300 g/ha for applications in foliar treatment. The dose of active material applied is generally and advantageously between 2 and 200 g per 100 kg of seed, preferably between 3 and 150 g per 100 kg of seed in the case of seed treatments. It is clearly understood that the doses indicated above are given as illustrative examples of the invention. A person skilled in the art will know how to tailor the application doses according to the nature of the crop to be treated.

The fungicidal composition according to the present invention may also be used in the treatment of genetically modified plants with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

Among the genes which give the transformed plants new agronomic properties, mention may be made of genes which impart a tolerance to certain herbicides, those which impart a resistance to certain insects, those which impart a tolerance to certain diseases, etc. Such genes are described in particular in patent applications WO 91/02071 and WO 95/06128.

Among the genes which impart a tolerance to certain herbicides, mention may be made of the Bar gene imparting tolerance to bialophos, the gene encoding a suitable EPSPS imparting a resistance to herbicides having EPSPS as target, such as glyphosate and its salts (U.S. Pat. Nos. 4,535,060, 4,769,061, 5,094,945, 4,940,835 5,188,642, 4,971,908, 5,145,783, 5,310,667, 5,312,910, 5,627,061, 5,633,435 and FR 2 736 926), the gene encoding glyphosate oxidoreductase (U.S. Pat. No. 5,463,175) or a gene encoding an HPPD imparting a tolerance to herbicides having HPPD as target, such as isoxazoles, in particular isoxafutol (FR 95/06800 and FR 95/13570), diketonitriles (EP-A-0 496 630 and EP-A-0 496 631) or triketones, in particular sulcotrioine (EP-A-0 625 505, EP-A-0 625 508 and U.S. Pat. No. 5,506,195). Such genes encoding an HPPD imparting a tolerance to herbicides having HPPD as target are disclosed in patent application WO 96/38567. In the case of genes encoding EPSPS or HPPD, and more particularly for the above genes, the sequence encoding these enzymes is advantageously preceded by a sequence encoding a transit peptide, in particular for the transit peptide known as optimized transit peptide, disclosed in patent U.S. Pat. No. 5,510,471.

Among the genes imparting novel insect-resistance properties, mention will be made more particularly of the genes encoding the Bt proteins which are widely described in the literature and well known to those skilled in the art. Mention will also be made of the genes encoding proteins extracted from bacteria such as Photorabdus (WO 97/17432 and WO 98/08932).

Among the genes imparting novel disease-resistance properties, mention will be made in particular of the genes encoding chitinases, glucanases and oxalate oxidase, all these proteins and their coding sequences being widely described in the literature, or genes encoding antibacterial and/or antifungal peptides, in particular 10 cysteine-rich peptides containing less than 100 amino acids, such as plant thionines or defensines, and more particularly lytic peptides of all origins comprising one or more disulphide bridges between the cysteines and regions comprising basic amino acids, in particular the following lytic peptides: androctonine (WO 97/30082 and PCT/FR98/01814, filed on 18 Aug. 1998) or drosomicin (PCT/FR98/01462, filed on 8 Jul. 1998). Mention will also be made of the genes encoding fungal elicitor peptides, in particular the elicitins (Kamoun et al., 1993; Panabières et al., 1995).

Among the genes which modify the constitution of modified plants, mention may be made in particular of genes which modify the content and quality of certain essential fatty acids (EP-A-0 666 918) or the content and quality of proteins, in particular in the leaves and/or seeds of the said plants. Mention will be made in particular of the genes encoding proteins that are rich in sulphur-containing amino acids (WO 98/20133; WO 97/41239; WO 95/31554; WO 94/20828 and WO 92/14822).

The fungicidal composition according to the present invention may, in particular, be used to the treatment of genetically modified plants comprising a heterologous gene, which gives the plant disease-resistance properties. The heterologous gene preferentially gives the genetically modified plant a spectrum of activity that is complementary to the spectrum of activity of the compounds according to the invention. According to the invention, the expression "complementary spectrum" means a spectrum of activity for the heterologous gene which is different from the spectrum of activity of the compounds according to the invention, or a spectrum of activity relating to identical infectious agents but allowing an identical or improved control for lower application doses of compounds according to the invention.

The compositions according to the present invention may also be used used to curatively or preventively treat human and animal fungal diseases such as, for example, mycoses, dermatoses, trichophyton diseases and candidiases or diseases caused by *Aspeigilhls* spp., for example *Aspergillis fumigatus*.

The aspects of the present invention will now be illustrated with reference to the following tables of compounds and examples. The following Tables I to III illustrate in a non-limiting manner examples of fungicidal compounds according to the present invention. In the following Examples, "MP" signifies "melting point" and is expressed in ° Celsius (° C.). M+1 (or M−1) means the molecular ion peak, plus or minus 1 a.m.u. (atomic mass units) respectively, as observed in mass spectroscopy.

TABLE I example of formula I-A:

[Structure diagram of formula I-A]

| N° | X | X1 | X2 | J | Q1 | Q2 | Mol. Ion | Melting point |
|---|---|---|---|---|---|---|---|---|
| A-1 | H | H | H | O | [p-phenylene] | [p-(OC6H4CF3)] | | |
| A-2 | H | H | H | S | [p-phenylene] | [p-(OC6H4CF3)] | 432 | M+1= |
| A-3 | H | H | H | S | [p-phenylene] | [m-(OC6H4CF3)] | 432 | M+1= |

TABLE I-continued
example of formula I-A:
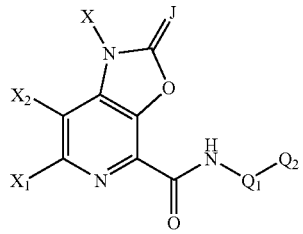
| N° | X | X1 | X2 | J | Q1 | Q2 | Mol. Ion | Melting point |
|---|---|---|---|---|---|---|---|---|
| A-4 | 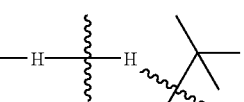 | —H | —H | O | 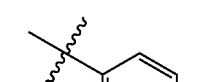 |  | M + 1 = 430 | |
TABLE II
example of formula I-B:
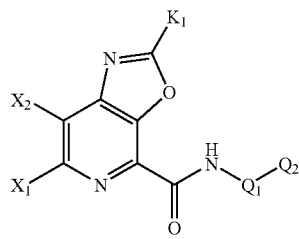
| N° | X1 | X2 | K1 | Q1 | Q2 | Mol. Ion | Melting point |
|---|---|---|---|---|---|---|---|
| B-1 | —H | —H |  |  | 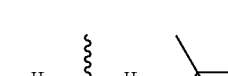 | M + 1 = 456 | |
| B-2 | —H | —H | 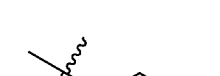 | 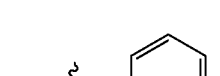 |  | M + 1 = 456 | |
| B-3 | —H | —H |  | 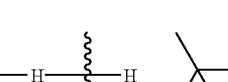 | 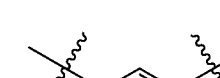Br | M + 1 = 374 | |

TABLE II-continued
example of formula I-B:
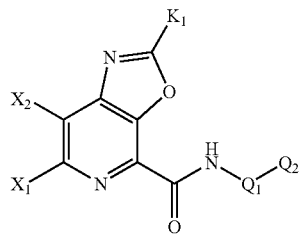
| N° | X1 | X2 | K1 | Q1 | Q2 | Mol. Ion | Melting point |
|---|---|---|---|---|---|---|---|
| B-4 | H | H | tBu | 1,4-phenylene | O-C6H4-4-CF3 | M+1 = 442 | |
| B-5 | H | H | tBu | 1,4-phenylene | O-C6H4-3-CF3 | M+1 = 442 | |
| B-6 | H | H | tBu | 1,3-phenylene | CH2Br | M+1 = 360 | |
| B-7 | H | H | iPr | 1,4-phenylene | O-C6H4-4-CF3 | M+1 = 456 | |
| B-8 | H | H | iPr | 1,4-phenylene | O-C6H4-3-CF3 | M+1 = 456 | |
| B-9 | H | H | iPr | 1,3-phenylene | CH2Br | M+1 = 374 | |
| B-10 | H | H | SMe | 1,4-phenylene | O-C6H4-4-CF3 | M+1 = 446 | |

TABLE II-continued example of formula I-B:

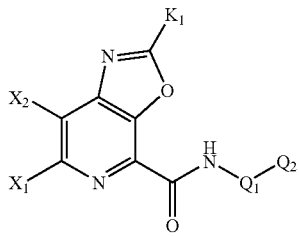

| N° | X1 | X2 | K1 | Q1 | Q2 | Mol. Ion | Melting point |
|---|---|---|---|---|---|---|---|
| B-11 | —H | —H | —S-iPr | -C6H4- | -C6H4-O-C6H4-CF3 | F F F | M + 1 = 474 |
| B-12 | —H | —H | —N(Et)2 | -C6H4- | -C6H4-O-C6H4-CF3 | F F F | M + 1 = 471 |

EXAMPLES OF PROCESS FOR PREPARATION OF THE COMPOUNDS OF GENERAL FORMULA (I)

Example A

Preparation of Compound of General Formula (I-A) n° A-1

1.3 g (3.3 mmol) of 4-Amino-3-hydroxy-N-para-[4-(trifluoromethyl)phenoxy]-phenylpicolinamide (prepared according to the method described in WO 0149666) in 20 mL of triethyl orthoformate with a catalytic amount of p-toluene sulphonic acid are heated under reflux for 3 hours. After cooling, the triethyl orthoformate was evaporated and the residue chromatography on silica gel. There is obtained 250 mg of a yellow solid (M+1=400).

Example B

Preparation of Compound of General Formula (I-B) n° B-3

To a solution of 180 mg (1 mmol) of 4-azido-3-hydroxy picolinic acid (prepared according to the method described in WO 0149666) in 2 ml of dichloromethane at 0° C. is added 0.4 ml (3 mmol) of triethylamine, followed by 0.27 ml (2.2 mmol) of pyvaloyl chloride. The resulting solution is stirred at room temperature for 1 hrs and 0.1 ml (0.9 mmol) of 3-bromoaniline is added. The reaction mixture is stirred at room temperature overnight, washed with brine, dried and solvent evaporated. 85 mg (0.2 mmol) of the residue is dissolved in 5 ml of tetrahydrofuranne. To this solution is added 480 mg (0.4 mmol) of PS-PPh$_3$. The reaction mixture is stirred at room temperature for 2 days, and filtered off. The resin is washed, and the filtrate is solvent evaporated. Purification of the residue on silica give 35 mg (44% yield) of a cream solid (M+1=374).

EXAMPLES OF BIOLOGICAL ACTIVITY OF THE COMPOUNDS OF THE INVENTION

Example 1

In Vivo Test on *Alternaria Brassicae* (Leaf Spot of Crucifers)

An aqueous suspension, at a concentration of 1.5%, of the active material tested is obtained by grinding it finely in a formulation of concentrated suspension type. This aqueous suspension is then diluted in water so as to obtain the desired active material concentration. Radish plants (Pernot variety) in starter cups, sown on a 50/50 peat soil-pozzolana substrate and grown at 18-20° C., are treated at the cotyledon stage by spraying with the aqueous suspension described above. Plants, used as controls, are treated with an aqueous solution not containing the active material.

After 24 hours, the plants are contaminated by spraying them with an aqueous suspension of *Alternaria brassicae* spores (40,000 spores per cm$^3$). The spores are collected from a 12-13 day-old culture. The contaminated radish plants are incubated for 6-7 days at about 18° C., under a humid atmosphere. Grading is carried out 6 to 7 days after the contamination, in comparison with the control plants. Under these conditions, good (at least 50%) or total protection is observed at a dose of 500 g/ha with a number of compounds of the present invention.

Example 2

In Vivo Test on *Septoria Nodorum* (Wheat Glume Blotch)

An aqueous suspension, at a concentration of 1.5%, of the active material tested is obtained by grinding it finely in a formulation of concentrated suspension type. This aqueous suspension is then diluted in water so as to obtain the desired active material concentration.

Wheat plants (Scipion variety) in starter cups, sown on a 50/50 peat soil-pozzolana substrate and grown at 12° C., are treated at the 1-leaf stage (10 cm tall) by spraying them with the aqueous suspension described above. Plants, used as controls, are treated with an aqueous solution not containing the active material. After 24 hours, the plants are contaminated by spraying with an aqueous suspension of *Septoria nodorum* spores (500,000 spores per $cm^3$). The spores are collected from a seven-day-old culture. The contaminated wheat plants are incubated for 72 hours at about 18° C., under a humid atmosphere, and then for 14 days at 90% relative humidity.

Grading is carried out 15 to 20 days after contamination, in comparison with the control plants. Under these conditions, good (at least 50%) or total protection is observed, at a dose of 500 g/ha, with a number of compounds of the present invention.

Example 3

In Vivo Test on *Erisyphe graminis* f. sp. *tritici* (Wheat Powdery Mildew)

An aqueous suspension, at a concentration of 1.5%, of the active material tested is obtained by grinding it finely in a formulation of concentrated suspension type. This aqueous suspension is then diluted in water so as to obtain the desired active material concentration. Wheat plants (Audace variety) in starter cups, sown on 50/50 peat soil-pozzulana substrate and grown at 12° C., are treated at the 1-leaf stage (10 cm tall) by spraying with the aqueous suspension described above. Plants, used as controls, are treated with an aqueous solution not containing the active material. After 24 hours, the plants are contaminated by dusting them with *Erisyphe graminis* f. sp. *tritici* spores, the dusting being carried out using diseased plants.

Grading is carried out 7 to 14 days after the contamination, in comparison with the control plants. Under these conditions, good (at least 50%) or total protection is observed, at a dose of 500 g/ha, with a number of compounds of the present invention.

Example 4

In Vivo Test on *Septoria Tritici* (Leaf Spot of Wheat)

An aqueous suspension, at a concentration of 1.5%, of the active material tested is obtained by grinding it finely in a formulation of concentrated suspension type. This aqueous suspension is then diluted in water so as to obtain the desired active material concentration. Wheat plants (Scipion variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Septoria tritici* spores (500,000 spores per mL). The spores are collected from a 15-day-old culture and are suspended in a nutrient solution composed of:

1.5 g/L of gelatin
  0.5 g/L of sodium oleate
  24 g/L of PDB

The contaminated wheat plants are incubated for 72 hours at about 20° C. and at 100% relative humidity, and then for 15 days at 80% relative humidity.

Grading is carried out 15 to 20 days after the contamination, in comparison with the control plants. Under these conditions, good (at least 50%) protection is observed, at a dose of 500 g/ha, with a number of compounds of the present invention.

Example 5

In Vivo Test on *Drechslera Teres* (Barley Net Blotch)

An aqueous suspension, at a concentration of 1.5%, of the active material tested is obtained by grinding it finely in a formulation of concentrated suspension type. This aqueous suspension is then diluted in water so as to obtain the desired active material concentration. Barley plants (Express variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Dreschslera teres* spores (12,000 spores per mL). The spores are collected from a 12-day-old culture. The contaminated wheat plants are incubated for 24 hours at about 20° C. and at 100% relative humidity, and then for 12 days at 80% relative humidity.

Grading is carried out 12 days after the contamination, in comparison with the control plants. Under these conditions, good (at least 50%) protection is observed, at a dose of 500 g/ba, with a number of compounds of the present invention.

Example 6

In Vivo Test on *Rhynchosporium secalis* (Barley Leaf Scald)

An aqueous suspension, at a concentration of 1.5%, of the active material tested is obtained by grinding it finely in a formulation of concentrated suspension type. This aqueous suspension is then diluted in water so as to obtain the desired active material concentration. Barley plants (Express or Barrack variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Rhynchosporium secalis* spores (800,000 spores per mL). The contaminated wheat plants are incubated for 48 hours at about 20° C. and at 100% relative humidity, and then for 12/14 days at 80% relative humidity. Grading is carried out 12/14 days after the contamination, in comparison with the control plants. Under these conditions, good (at least 50%) protection is observed, at a dose of 500 g/ha, with a number of compounds of the present invention.

Example 7

In Vivo Test on *Pucccinia recondita* (Wheat Brown Rust)

An aqueous suspension, at a concentration of 1.5%, of the active material tested is obtained by grinding it finely in a formulation of concentrated suspension type. This aqueous suspension is then diluted in water so as to obtain the desired active material concentration. Wheat plants (Scipion variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Puccinia recondita* spores (150,000 spores per mL). The contaminated wheat plants are incubated for 24 hours at about 20° C. and at 100% relative humidity, and then for 10 days at 70% relative humidity.

Grading is carried out 10 days after the contamination, in comparison with the control plants. Under these conditions, good (at least 50%) protection is observed, at a dose of 500 g/ha, with a number of compounds of the present invention.

Example 8

In Vivo Test on *Botrytis Cinerea* (Cucumber Grey Mould)

An aqueous suspension, at a concentration of 1.5%, of the active material tested is obtained by grinding it finely in a formulation of concentrated suspension type. This aqueous suspension is then diluted in water so as to obtain the desired active material concentration. Cucumber plants (Marketer variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material;

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatin
50 g/L of cane sugar
2 g/L of NH4NO3
1 g/L of KH2PO4

The contaminated cucumber plants are settled for 5/7 days in a climatic room at 15-11° C. (day/night) and at 80% relative humidity.

Grading is carried out 5/7 days after the contamination, in comparison with the control plants. Under these conditions, good (at least 50%) protection is observed, at a dose of 500 g/ha, with a number of compounds of the present invention.

What is claimed is:

1. A compound of the general formula (I):

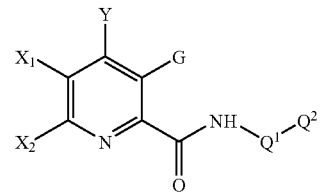

in which:

Y and G together with carbon atoms 3 and 4, form a 5 or 6 member ring selected from the group consisting of the following structures A to F:

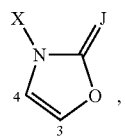

A

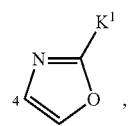

B

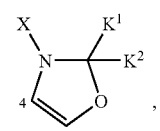

C

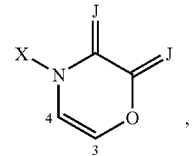

D

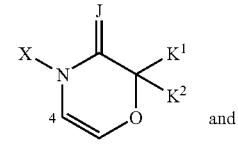

E and

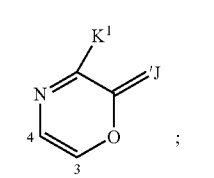

F

;

in which:

each J is independently selected from the group consisting of oxygen and sulphur;

X is selected from the group consisting of hydrogen, $C_1$-$C_4$ alkyl and $C_1$-$C_4$ halogenoalkyl;

$K^1$ and $K^2$ are independently selected from the group consisting of hydrogen, halogen, $C_1$-$C_4$ alkyl, $C_1$-$C_4$ halogenoalkyl, $C_1$-$C_4$ alkoxyalkyl, $C_1$-$C_4$ alkythioalkyl, —$OR^1$, —$SR^1$, —$SOR^1$, —$SO_2R^1$, —$NHR^3$, —$NR^1R^3$ and

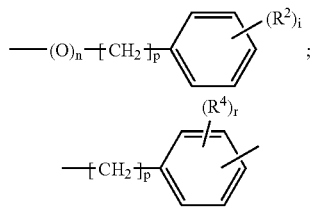

$X_1$ and $X_2$ are independently selected from the group consisting of hydrogen, halogen, —$CF_3$, a cyano group and a nitro group;

$Q^1$ is selected from the group consisting of —$(CH_2)_q$—,

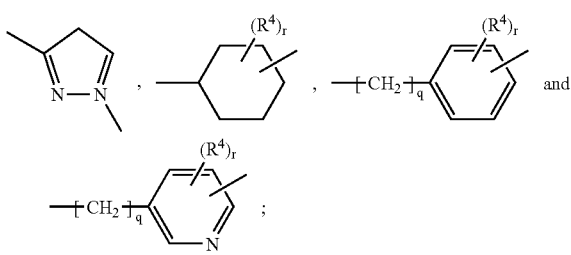

$Q^2$ is selected from the group consisting of —$(O)_n$—$R^5$, a cyano group,

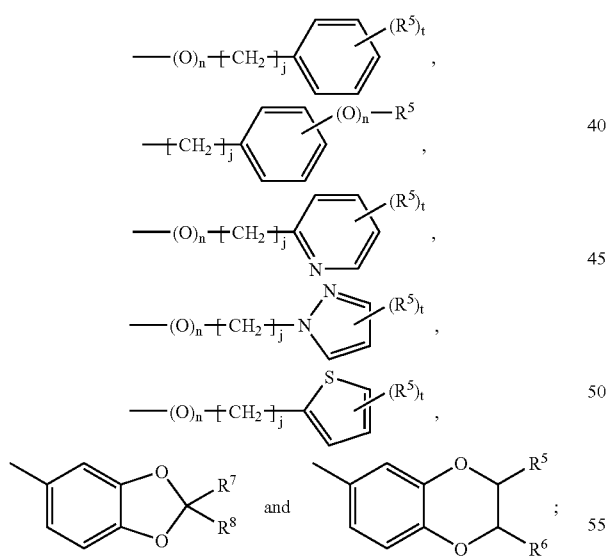

$R^1$ is selected from the group consisting of hydrogen, $C_1$-$C_4$ alkyl, $C_1$-$C_4$ halogenoalkyl, alkenyl, alkynyl, heterocyclyl, —CH=O, —(C=O)-alkyl and —(C=O)-Oalkyl;

$R^2$ is selected from the group consisting of halogen, $C_1$-$C_4$ alkyl, $C_1$-$C_4$ alkoxy, $C_1$-$C_4$ halogenoalkyl and aryl;

$R^3$ is selected from the group consisting of hydrogen, $C_1$-$C_4$ alkyl, $C_1$-$C_4$ halogenoalkyl, $C_1$-$C_4$ alkoxy, alkenyl, alkynyl, heterocyclyl, —CH=O, —(C=O)-alkyl and —(C=O)-Oalkyl;

$R^4$ is selected from the group consisting of halogen, $C_1$-$C_4$ alkyl and $C_1$-$C_4$ alkoxyalkyl;

$R^5$ and $R^6$ are independently selected from the group consisting of hydrogen, halogen, $C_1$-$C_4$ alkyl, and $C_1$-$C_4$ halogenoalkyl;

$R^7$ and $R^8$ are independently selected from the group consisting of hydrogen and halogen;

n is 0 or 1;

i, j, p, q and t are independently chosen as being 0,1,2,3 or 4;

r is 0, 1, 2 or 3;

as well as any optional N-oxides, optical isomers, enantiomers and/or diastereoisomers, tautomeric forms, and salts of the compounds of formula (I) as here-above defined.

2. The compound of claim 1, wherein $X^1$ and $X^2$ represent a hydrogen atom.

3. The compound of claim 1, wherein Y and G with carbon 3 and 4 form a ring chosen from structures A to C.

4. The compound of claim 1, wherein $Q^1$ is selected from the group consisting of:

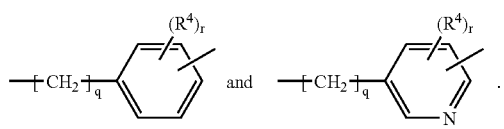

5. The compound of claim 1, wherein:
$X^1$ and $X^2$ each represent hydrogen,
Y and G together with carbon 3 and 4, form a 5 member ring chosen from structures A to C, and
$Q_1$ is selected from the

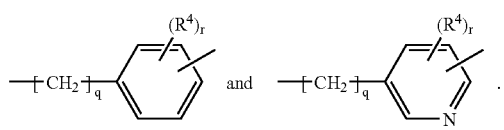

6. The compound of claim 5, wherein:
$X^1$ and $X^2$ each represent hydrogen,
Y and G together with carbon 3 and 4, form a 5 member ring chosen from:

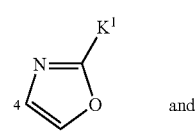

in which:
X is hydrogen
$K^1$ and $K^2$ are independently selected from the group consisting of hydrogen, alkyl and N,N-dialkylamino; and $Q^1$ is selected from the group consisting of

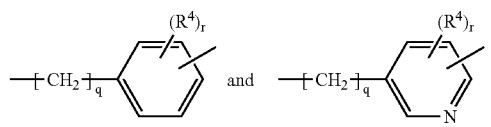

7. The compound of claim 6, wherein:
Y and G together with carbon 3 and 4, may form a 5 member ring of formula A:

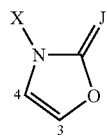

in which:
J is oxygen,
X is hydrogen; and
$Q^1$ is selected from the group consisting of

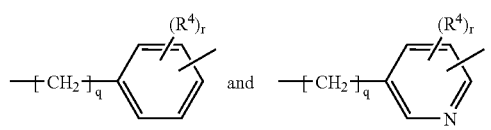

8. Process for preparing the compound according to claim 1 which comprises reacting a compound of general formula (II)

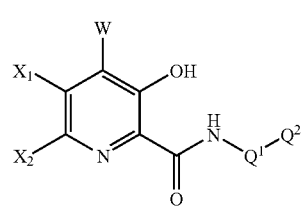

in which $X^1$, $X^2$, $Q^1$ and $Q^2$ are as defined above and W is $NH_2$ or $N_3$, with a phosgene or thiophosgene solution, an acid halide or a ketone in the presence is of solvent.

9. Process according to claim 8 for preparing the compound of general formula (I-A):

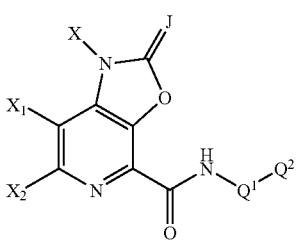

in which J, X, $X^1$, $X^2$, $Q^1$ and $Q^2$ are as defined above, characterised in that it comprises reacting the compound of general formula (II) where W is $NH_2$ in an apolar aprotic solvent.

10. Process according to claim 9, characterised in that the solvent is an hydrocarbon solvent such as benzene and toluene and that it is carried out at reflux or at a temperature of between 20° C. and 200° C.

11. Process according to claim 8 for preparing the compound of general formula (I-B):

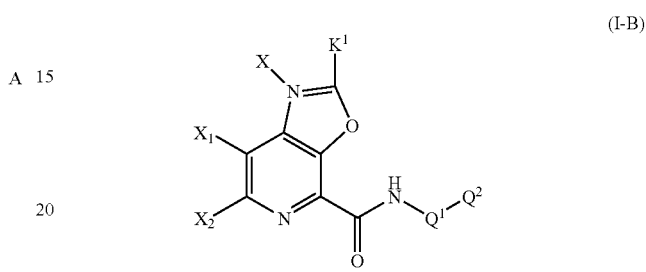

in which $K^1$, X, $X^1$, $X^2$, $Q^1$ and $Q^2$ are as defined above, characterised in that it comprises reacting the compound of general formula (II) where W is $NH_2$ with acid chloride and a base such as triethylamine in a chlorinated solvent, the subsequent reduction of the intermediate being obtained with a reducing agents such as triphenyl phosphine or sodium borohydride in an alcoholic solvent such as ethanol or THF.

12. Process according to claim 11, characterised in that the solvent is dichloromethane and that it is carried out at room temperature or at a temperature between −10° C. and +50° C., followed by addition of an amine.

13. Process according to claim 8 for preparing the compound of general formula (I-C):

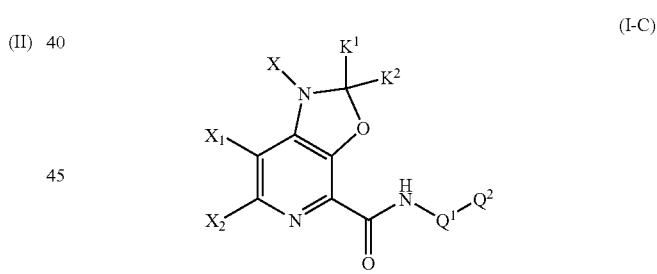

in which X, $K^1$, $K^2$, $X^3$, $Q^1$ and $Q^2$ are as defined above, characterised in that it comprises reacting the compound of general formula (II) in which W is $NH_2$ with alkyl or aryl ketone in an apolar aprotic solvent.

14. Process according to claim 13, characterised in that the solvent is an hydrocarbon solvent such as benzene and toluene and that it is carried out at reflux or at a temperature of between 20° C. and 200° C.

15. A fungicidal composition comprising an effective amount of a compound according to claim 1 and an agriculturally acceptable support.

16. The fungicidal composition of claim 15 further comprising a surfactant.

17. The flungicidal composition of claim 15, comprising from 0.05% to 99% by weight of active material.

18. Method for preventively or curatively combating the phytopathogenic fungi of crops, characterised in that an effective and non-phytotoxic amount of a composition according to claim 15 is applied to the plant seeds or to the plant leaves and/or to the fruits of the plants or to the soil in which the plants are growing or in which it is desired to grow them.

19. Method according to claim 18, in which the dose of active material applied is between 10 g and 800 g of active material per hectare, in the case of foliar treatments.

20. Method according to claim 19, in which the dose of active material applied is between 50 g and 300 g of active material per hectare in the case of foliar treatments.

21. Method according to claim 18, in which the dose of active material applied is between 2 and 200 g of active material per 100 kg of seed, in the case of seed treatments.

22. The compound of claim 2 wherein Y and G with carbon 3 and 4 form a ring selected from the group consisting of structures A to C.

23. The fungicidal composition of claim 16, comprising from 0.05% to 99% by weight of active material.

24. The compound of claim 1 wherein the compound of the general formula (I) is selected from the group consisting of:

(A) compounds and intermediates of the formula:

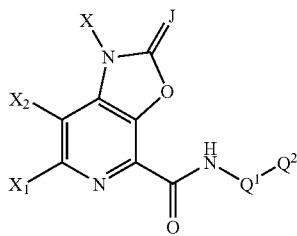

wherein
$X$, $X_1$, and $X_2$ are hydrogen;
J is oxygen or sulphur;
$Q^1$ is

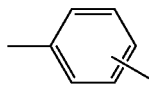

$Q^2$ is

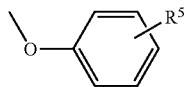

where $R^5$ is $C_1$-$C_4$ halogenoalkyl; and (B) compounds and intermediates of the formula:

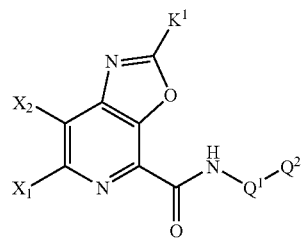

wherein
$X_1$ and $X_2$ are hydrogen;
$K^1$ is $C_1$-$C_4$ alkyl;
$Q^1$ is

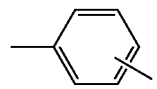

and
$Q^2$ is a halogen or

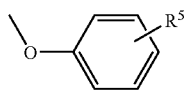

where $R^5$ is $C_1$-$C_4$ halogenoalkyl.

\* \* \* \* \*